United States Patent [19]

Ohki et al.

[11] Patent Number: 5,007,732
[45] Date of Patent: Apr. 16, 1991

[54] FLOW-CELL DEVICE

[75] Inventors: Hiroshi Ohki, Tsuchiura; Hideaki Kamohara; Ryo Miyake, both of Ibaraki, all of Japan

[73] Assignee: Hitachi, Ltd., Japan

[21] Appl. No.: 182,430

[22] Filed: Apr. 18, 1988

[30] Foreign Application Priority Data

Apr. 20, 1987 [JP] Japan .................................. 62-97130

[51] Int. Cl.$^5$ ....................... G01N 21/00; G01N 21/85
[52] U.S. Cl. ....................................... 356/73; 356/410; 356/39
[58] Field of Search ................... 356/73, 72, 353, 410, 356/337, 343, 39; 350/362; 250/257

[56] References Cited

U.S. PATENT DOCUMENTS

| | | | |
|---|---|---|---|
| 3,649,829 | 3/1972 | Randolph | 356/410 |
| 3,893,766 | 7/1975 | Hogg | 356/39 |
| 3,967,265 | 6/1976 | Jacob | 350/362 |
| 4,352,558 | 10/1982 | Eisert | 356/39 |
| 4,737,025 | 4/1988 | Steen | 356/73 |
| 4,781,459 | 11/1988 | Suzuki | 356/73 |

OTHER PUBLICATIONS

Review of Scientific Instruments, vol. 55, No. 9, Sep. 1984, pp. 1375-1400, New York, U.S.
The Journal of Histochemistry and Cytochemistry, vol. 25, No. 7, pp. 774-780.
Biophysical Journal, vol. 23, 1987, pp. 7-13.

*Primary Examiner*—Richard A. Rosenberger
*Assistant Examiner*—Hoa Pham
*Attorney, Agent, or Firm*—Antonelli, Terry, Stout & Kraus

[57] ABSTRACT

A sheath flow type flow-cell device for flow-cytometer which comprises a first inlet for sheath fluid, a flow passage communicated with the first inlet and contracted toward downstream, the flow passage having a substantially rectangular cross section, a straight capillary flow passage connected to the flow passage downstream thereof, the capillary flow passage having a substantially rectangular cross section, a second inlet for sample fluid, a nozzle communicating with the second inlet and opened within the flow passage in the same direction as the flow direction of the straight capillary flow passage, a discharge port provided at a terminal end of the straight capillary flow passage, and flow regulating means for regulating the flow of the sheath fluid in the straight capillary flow passage to be a laminar flow having a gradient of flow velocity.

9 Claims, 4 Drawing Sheets

FLOW-CELL DEVICE

BACKGROUND OF THE INVENTION

The present invention relates to a flow-cell device and, more particularly, to a flow-cell device suitable for use in cellular analysis of living bodies.

Hitherto, apparatus has been known for conducting cellular analysis of living bodies by causing cells extracted from a living body to flow in a flow-cell device while effecting photometry of the cells. In this apparatus, generally known as a flow-cytometer, a light beam is applied to cells in the suspension of cells and, on the basis of scattering light and fluorescence from the cells, the analyses of the sizes, shapes and other state of cells are conducted.

In operation of the flow-cytometer, in order to pour the suspension of cells through a capillary flow passage for measurement with stability and without clogging, a method has been adopted in which the suspension of cells is made to flow by being surrounded by physiological saline physiological SaH solution. The method will be described with reference to FIG. 10. FIG. 10 shows a concept of the method. In FIG. 10, the suspension of cells 1, namely, sample fluid is surrounded by the physiological saline 2, namely, sheath fluid. That is, sheath fluid flow is formed around sample fluid flow and the sample fluid flow becomes a laminar flow. The sample fluid and the sheath fluid are discharged from a discharge port 3 to the exterior.

This method is referred to as "sheath-flow method", and constitutes an effective measure in the cellular analysis, but involves the following disadvantages. Forces 4 as shown in FIG. 10 act on the cells in the suspension from the surfaces of the capillary flow passage surfaces and physiological saline, so that flat cells such as red carpuscles are oriented at random in the measuring portion, with the result that the measurement data of scattered light and fluorescence fluctuate undesirably.

Two measures have been taken for the purpose of overcoming these problems. One of these measures is to introduce a variation in the length-to-breadth ratio between the flow-contracting portion and the capillary flow passage as shown in FIG. 11, so as to vary the magnitudes of the forces acting on the flowing cells in the longitudinal and breadthwise directions, thereby to uniformly orient the flat cells. This method is discussed in the Journal of Histochemistry and Cytochemistry, Vol. 25, No. 7 (1977) pp. 774–780.

Another measure is to adopt a wedge-shaped form on the end of a nozzle 5 through which the suspension of cells (sample fluid) is discharged into the flow of the sheath fluid, as shown in FIGS. 12A and 12B. FIG. 12A is a perspective view of the nozzle 5. FIG. 12B is a sectional view of the flow-cell showing the state of flow of the sample fluid 1 and the sheath fluid 2 supplied from the nozzle 5. As shown in FIGS. 12A and 12B, by using a wedge-shaped form on the end of the nozzle 5, the sample fluid flow in the sheath fluid flow becomes flat. Therefore, it is possible to confine the flat cells in the flat flow of the sample fluid. This method is described in detail in "Biophysics Journal", Vol. 23 (1978) pp. 7–13.

The prior art techniques described involve the following problems. Namely, in the method of FIG. 11 relying upon variation of the length-to-breadth ratio of the cross-section of the flow-cell, the ratio between the forces acting on the cell in the longitudinal and breadthwise directions is constant, so that the cell receives rotational moment depending on the initial posture of the cell discharged from the nozzle. In consequence, the cells fail to be oriented in the same direction.

On the other hand, the known art relying upon wedge-shaped form of the suspension explained with reference to FIGS. 12A and 12B has a drawback in that the flattened flow of the suspension tends to be twisted in the form of a ribbon, even by a slight turbulence of the sheath fluid (physiological saline), with the result that the measurement of the flat cells in the constant direction is failed.

Obviously, the fact that the flat cells cannot be measured stably in flat positions impairs the precision of the data obtained through the measurement conducted at the photometry section.

SUMMARY OF THE INVENTION

Accordingly, an object of the present invention is to provide a flow-cell device which enables highly accurate photometry of cells even if the cells are flat.

According to the present invention, there is provided a sheath flow type flow-cell device for flow-cytometer comprising a first inlet for a sheath fluid; a flow passage communicated with the first inlet and contracted toward downstream, the flow passage having a substantially rectangular cross section; a straight capillary flow passage connected to the flow passage at downstream thereof, the capillary flow passage having a substantially rectangular cross section; a second inlet for sample fluid; a nozzle communicating with the second inlet and opened within the flow passage in the same direction as the flow direction of the straight capillary flow passage; a discharge port provided at a terminal end of the straight capillary flow passage; and flow regulating means for regulating the flow of the sheath fluid in the straight capillary flow passage to be a laminar flow having a gradient of flow velocity.

In an embodiment of the sheath flow type flow-cell device, the flow regulating means comprises a side wall of the capillary flow passage having a smooth surface and another side wall having a rough surface.

In another embodiment of the sheath flow type flow-cell device, the flow regulating means comprises a net member stretched across the flow passage upstream from the opening of the nozzle, the mesh of the net being minuter from a first side wall of said flow passage toward another side wall opposite to the first side wall.

In a further embodiment of a sheath flow type flow-cell device, the flow regulating means comprises a plurality of partition walls extended in the flow passage in the flow direction and dividing the flow passage into a plurality divided flow passages of the flow resistance of which are made gradually large from a first side wall of the flow passage toward another side wall opposite to the first side wall.

In the flow-cell device of the present invention, the flow of fluid in the capillary flow passage takes the form of parallel flows having a certain velocity gradient, i.e., the form of a sheared flow, so that the cells existing in the sheared flow are deformed to assume shapes symmetrical with respect to their axes, whereby the flat cells are oriented in the same posture, thus avoiding any fluctuation of the photometric data and, hence, assuring high precision of measurement.

DETAILED DESCRIPTION OF THE PREFERRED EMBODIMENTS

Figure 1:
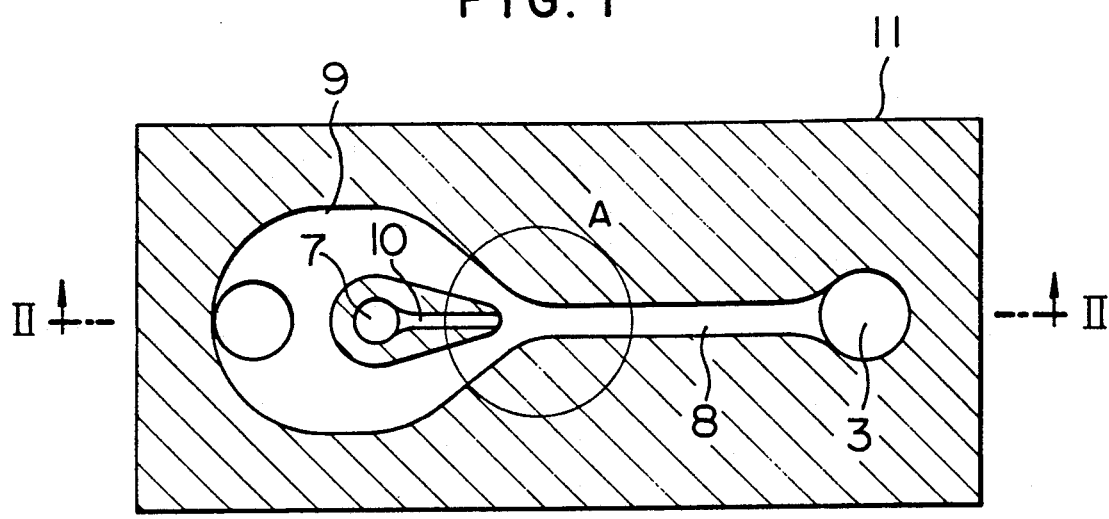
FIG. 1 is a sectional plan view of an embodiment of the flow-cell device in accordance with the present invention.
Figure 2:
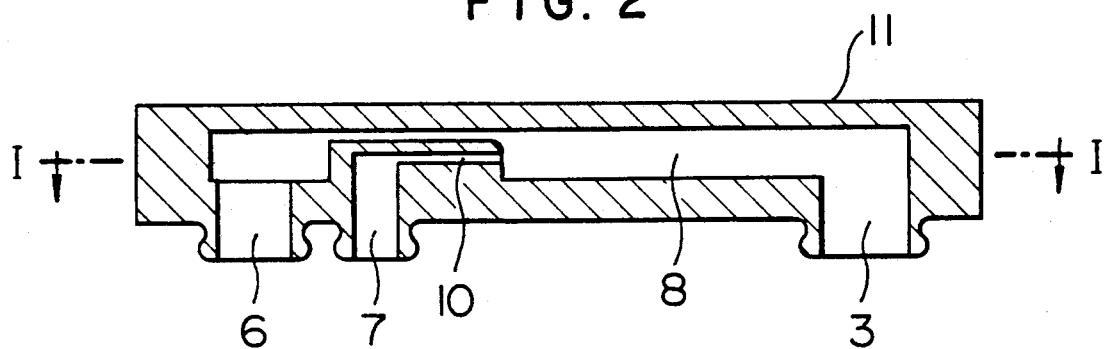
FIG. 2 is a sectional view taken along the line II—II of FIG. 1.
Figure 3:
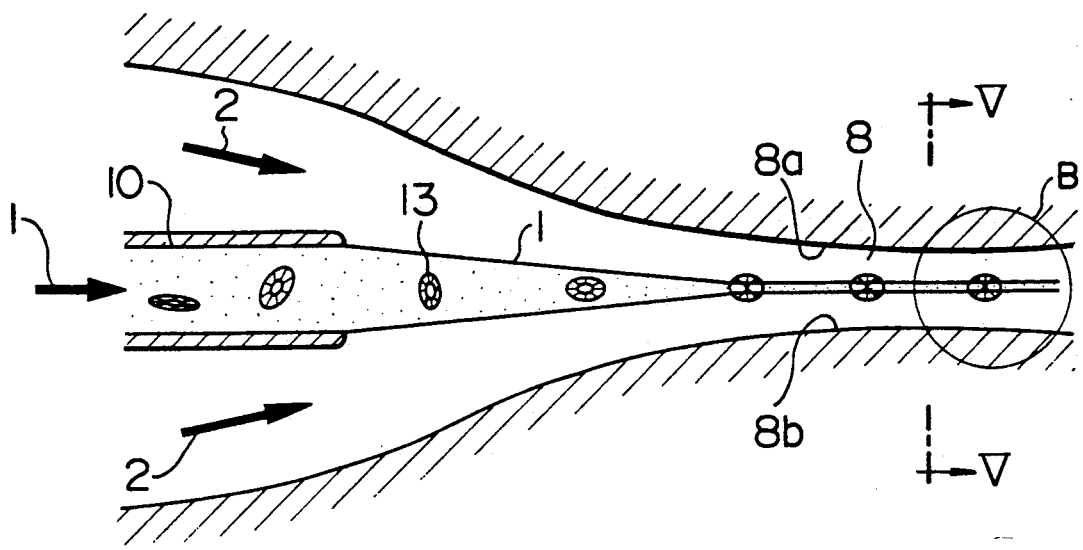
FIG. 3 is an enlarged view of a portion marked at A in FIG. 1.

Preferred embodiments of the present invention will be described hereinafter with reference to the accompanying drawings. FIGS. 1-5 show an embodiment of the flow-cell device of the invention. The flow-cell device has a first inlet 6 for sheath fluid 2, a second inlet 7 for suspension of cells 1 (referred to as "sample fluid", hereinafter), a flow passage 9 communicating with the first inlet 6 and contracting downward, a straight capillary flow passage 8 communicating with the flow passage 9 at an end of the latter, a discharge port 3 provided at a terminal end of the capillary flow passage 8, and a nozzle 10 opened in the flow passage 9. The nozzle 10 is opened in the same direction as the direction of flow of the sample fluid in the capillary flow passage 8. The capillary flow passage 8 and the flow passage 9 have substantially rectangular cross-sections. The top wall 15 and the bottom wall 16 of the capillary flow passage 8 are made transparent so that measuring light can pass therethrough.

The capillary flow passage 8 is provided with flow regulating means. Namely, one side wall 8a of the capillary flow passage has a smooth surface, while the other side wall 8b has a roughened surface. In consequence, the fluid flowing through the capillary flow passage 8 encounters comparatively small resistance at its portion adjacent to the smooth surface 8a and comparatively large resistance at its portion adjacent to the roughened surface 8b. The distance between the side wall 8a and the side wall 8b is usually as small as 50 μm to 500 μm. Therefore, the flow of the fluid in the capillary flow passage 8 forms a sheared flow. Namely, the flow of the fluid in the capillary flow passage 8 is a laminar flow having a velocity gradient pattern 14 shown in FIG. 4.

The operation of this embodiment is as follows.

Figure 4:
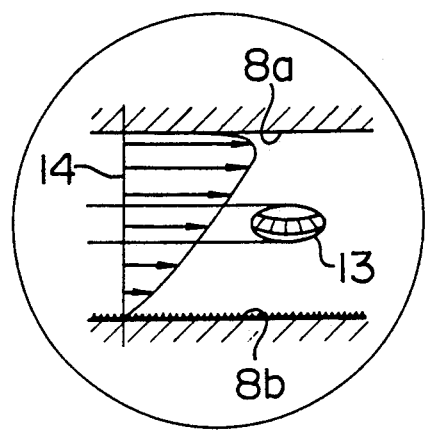
FIG. 4 is an enlarged view of a portion marked at B in FIG. 3.
Figure 5:
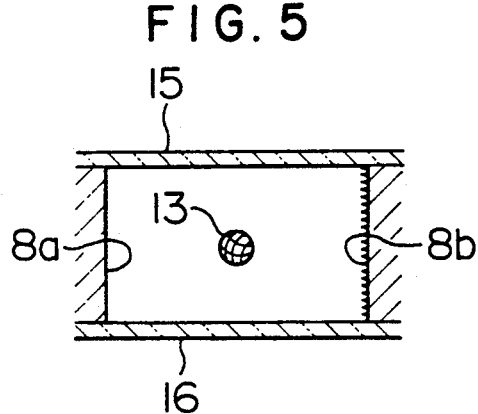
FIG. 5 is a sectional view taken along the line V—V of FIG. 3.

The nozzle 10 is supplied with a sample fluid 1 which is a suspension fluid including cells 13 to be examined. The sample fluid is fed under pressure so that a flow of the sample fluid occurs in the capillary flow passage 8 from the end of the nozzle 10. Meanwhile, a sheath fluid 2 is fed under pressure in the flow passage 9 around the nozzle 10. Thus, the sheath fluid 2 flows in such a manner that it surrounds or sheathes the sample fluid 1. At the same time, the flow passage 9 leading to the measuring section is contracted to a predetermined size. For these reasons, the sample fluid 1 is drastically contracted to form a contracted laminar flow. As a result, cells are made to pass through the measuring section in a one-by-one fashion. The flow of the fluid in the capillary flow passage 8 is a laminar flow having a velocity gradient, i.e., a sheared flow. The cell 13 subjected to the sheared flow, therefore, is deformed into a cell 13 which has a form symmetrical with respect to the axis thereof, as shown in FIG. 4. Thus, the cell 13 becomes to have a form resembling that of a Rugby ball with its longitudinal axis coinciding with the direction of the flow. As a result, all the cells, even if they may be flat, take the same posture when they pass through the measuring section, whereby any fluctuation of the measured data is avoided to ensure a high degree of precision of measurement.

Regarding the degree of smoothness of the surfaces of the side walls, the roughness of the smooth surface is not greater than 1/500 of the distance between the side wall surfaces, while the roughness of the roughened surface is preferably 1/20 or greater of the distance between the side wall surfaces. More specifically, the roughness of the smooth wall surface ranges between 1 S and 10 S, while the roughness of the roughened surface ranges between 100 S and 1000 S.

Figure 6:
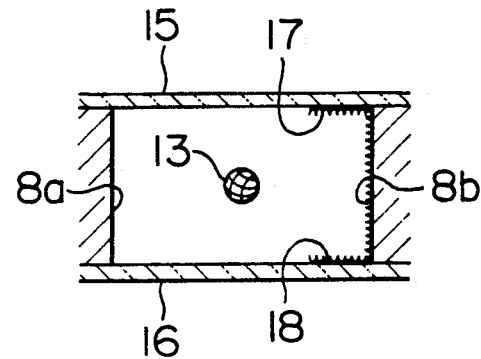
FIG. 6 is a sectional view showing the modification of the embodiment shown in FIG. 5.

FIG. 6 shows a modification of the embodiment described above. In this embodiment, the roughened surface extends to constitute parts of the top wall 15 and the bottom wall 16. With this arrangement, the laminar flow of the fluid in the capillary flow passage 8 can have a greater velocity gradient than that in the embodiment shown in FIG. 5. This means that the modification shown in FIG. 6 promotes the tendency for the cell to assume a form which is symmetrical with respect to its axis, as compared to the case of the embodiment shown in FIG. 5.

Obviously, the described embodiment of the present invention should be designed to enable measurement of scattered light and fluorescence through the transparent top wall 15 and the bottom wall 16. The width of the roughened regions 17, 18 on the top wall and the bottom wall, therefore, should be not greater than ⅓ that of the distance between the opposing side walls, in order to enable such measurement. It is also necessary that the optical system be adjusted so as to prevent incident light and the scattered light from impinging upon these regions.

In the embodiment shown in FIGS. 1 and 6, the smoothness of the smooth wall surfaces may be formed by polishing, plating or any other known suitable method. The roughening of the surfaces may be done by knurling or fine cutting or the like.

Figure 7:
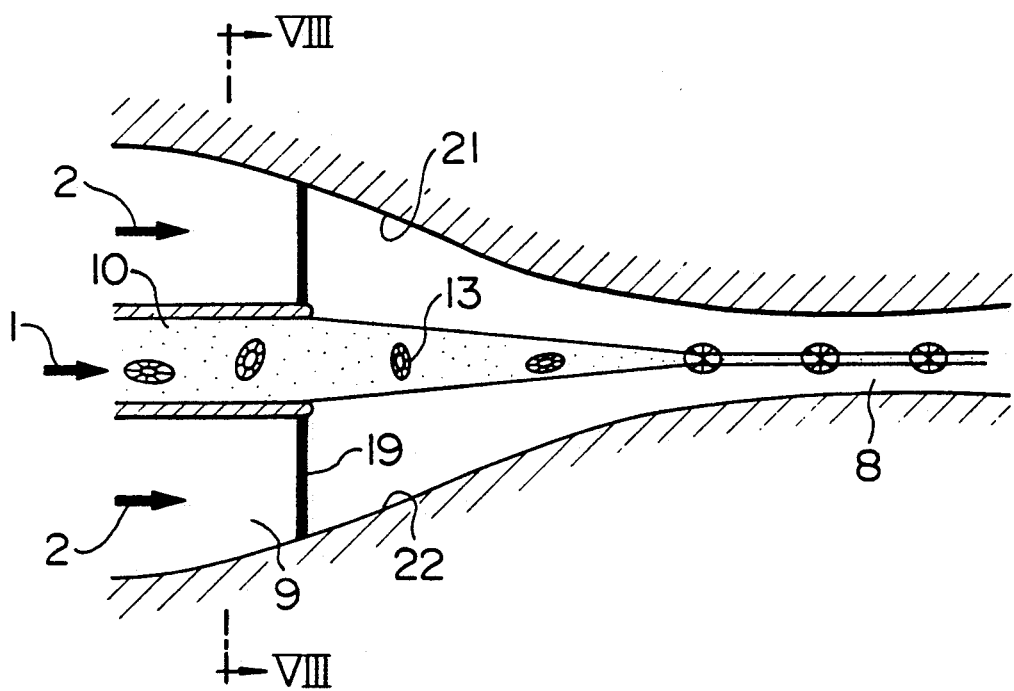
FIG. 7 is an enlarged view similar to that in FIG. 3, illustrating another embodiment of the flow-cell device in accordance with the present invention.
Figure 8:
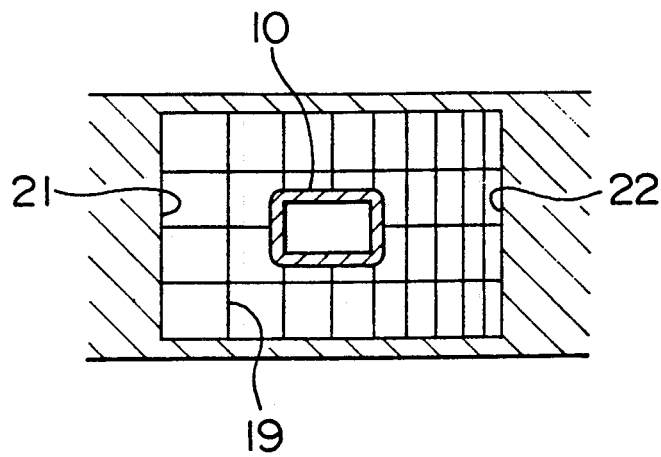
FIG. 8 is a sectional view taken along the line VIII—VIII of FIG. 7.

Another embodiment of the present invention will be described with reference to FIGS. 7 and 8. A net member 19 is disposed upstream from the opening of the nozzle 10 across the flow passage 9. The mesh of the net is so varied that it becomes finer from one of the side walls 21 towards the other side wall 22. In consequence, the sheath fluid flowing in the flow passage 9 encounters resistance which varies along the plane of the net member 19 in accordance with the variation of the mesh. In consequence, the fluid flowing in the capillary flow passage exhibits a flow velocity distribution pattern as shown in FIG. 4, thereby the cells 13 are deformed into a form which is symmetrical with respect to the axis thereof. In this embodiment, it is not preferred to dispose the net member 19 downstream from the end of the nozzle 10, because in such a case the cells 13 will be undesirably caught by the mesh of the net member 19 to hinder the measurement.

Figure 9:
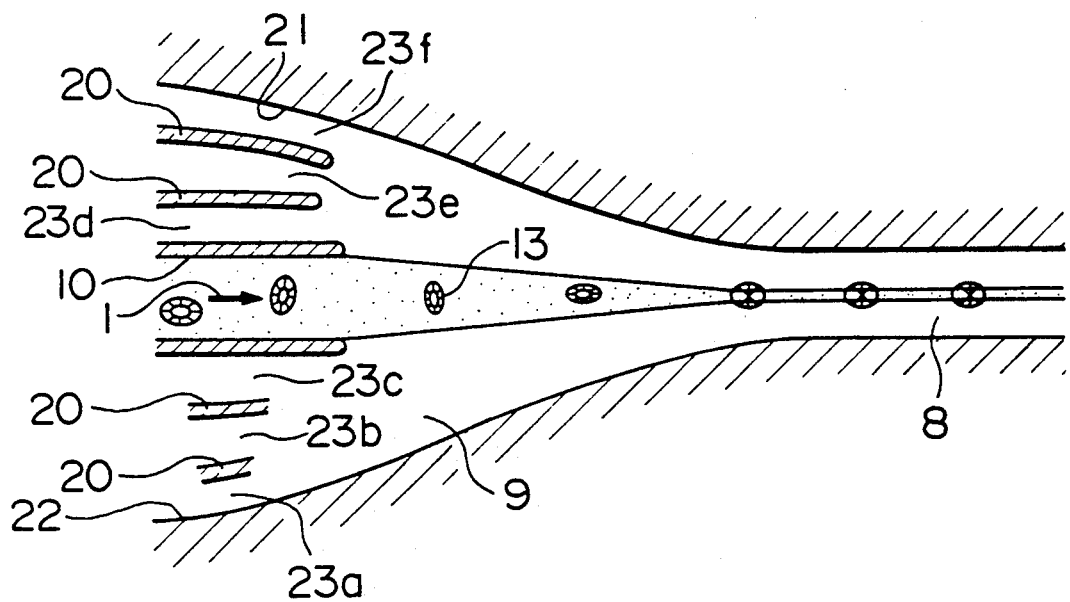
FIG. 9 is an enlarged view similar to that in FIG. 3, illustrating another embodiment of the flow-cell device in accordance with the present invention.
Figure 10:
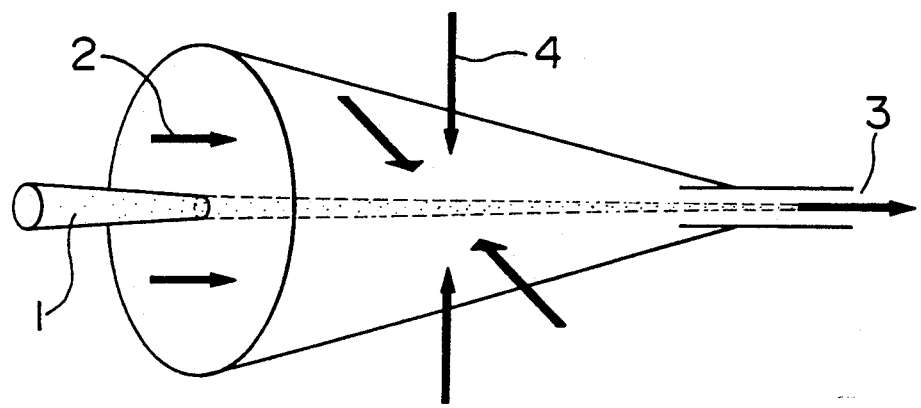
FIG. 10 is a schematic illustration of a prior art flow-cell device.
Figure 11:
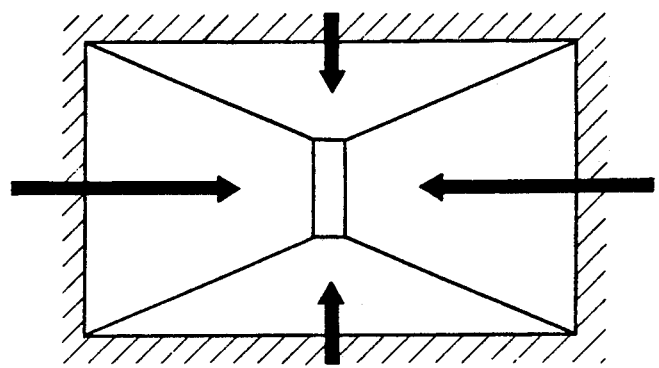
FIG. 11 is a sectional view of another prior art flow-cell device.
Figure 12A:
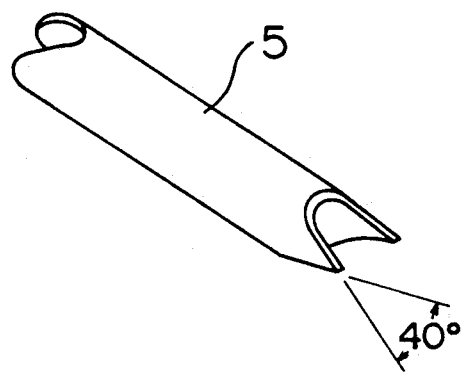
FIG. 12A is a perspective view of a nozzle used in a prior-art flow-cell device.
Figure 12B:
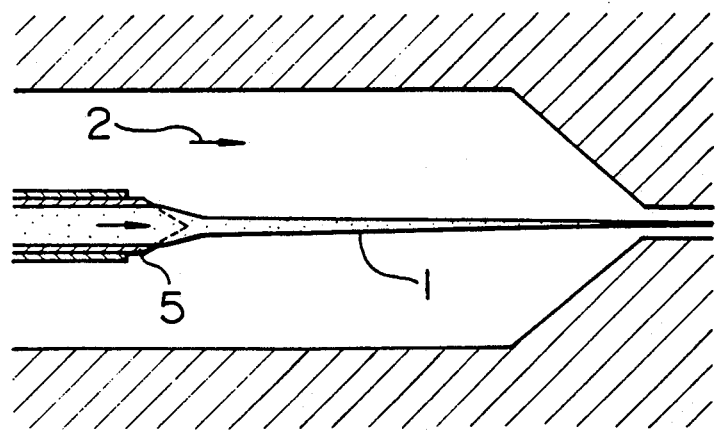
FIG. 12B is a sectional view of the flow cell device incorporating the nozzle shown in FIG. 12A.

Another embodiment of the present invention will be described hereinafter with reference to FIG. 9.

In the embodiment, a plurality of partition walls 20 extending in the flow direction of the flow passage 9 are provided in the flow passage 9. The partition walls 20 divide the flow passage 9 into a plurality of divided flow passages. In the illustrated case, the flow passage 9 is divided into six divided flow passages 23a, 23b, 23c, 23d, 23e, 23f. The length of the divided flow passages are made longer as the divided flow passages locate near approach the side wall 21. Therefore, the flow resistance of the divided flow passages 23a, 23b, 23c, 23d, 23e, 23f are larger as they approach the side wall 21, whereby a flow velocity distribution pattern of the sheath fluid as shown in FIG. 4 is obtained. As a result, it is possible to deform the cells in the sample fluid flowing through the capillary flow passage 8 into the form which is symmetrical with respect to its longitudinal axis. The number of the partition walls may be varied as desired.

As described hereinbefore, according to the present invention, the fluid flowing through the capillary flow passage forms a sheared flow over the entire cross-section of the capillary flow passage. As a result, the cells in the sample fluid is deformed into a form which is in symmetry with respect to its axis. This ensures that all cells, even if they may be flat, are oriented in the constant direction so as to eliminate any fluctuation of the measured data.

We claim:

1. A sheath flow type flow-cell device for a flow-cytometer comprising:
    a first inlet for sheath fluid,
    a flow passage communicating with said first inlet and contracted toward downstream, said flow passage having a substantially rectangular cross section,
    a straight capillary flow passage connected to said flow passage downstream thereof, said capillary flow passage having a substantially rectangular cross section,
    a second inlet for sample fluid,
    a nozzle communicating with said second inlet and opened within said flow passage in the same direction as the flow direction of said straight capillary flow passage,
    a discharge port provided at a terminal end of said straight capillary flow passage, and
    flow regulating means for regulating the flow of said sheath fluid in said straight capillary flow passage to be a laminar flow having a gradient of flow velocity, wherein said straight capillary flow passage has opposing first and second side walls connected by top and bottom walls and wherein said flow regulating means comprises said second said wall having a rougher surface than a surface of said first said wall.

2. A sheath flow type flow-cell device as claimed in claim 1, wherein said flow regulating means further includes a part of said top wall and a part of said bottom wall of said capillary flow passage having rough surface portions adjacent to said second side wall.

3. A sheath flow type flow-cell device as claimed in claim 2, wherein the width of said rough surfaces of said top and bottom walls from said second side wall is ⅛ and under of a distance between said first side wall and said second side wall.

4. A sheath flow type flow-cell device as claimed in claim 1, wherein the surface roughness of said surface of said first side wall is 1/500 and under of a distance between said first side wall and said second side wall and the surface roughness of said surface of said second side wall is 1/20 and over of said distance.

5. A sheath flow type flow-cell device as claimed in claim 1, wherein the surface roughness of said surface of said first side wall exists from 1 S to 10 S and the surface roughness of said surface of said second side wall exists from 100 S to 1000 S.

6. A sheath flow type flow-cell device for a flow-cytometer comprising:
    a first inlet for sheath fluid,
    a flow passage communicating with said first inlet and contracted toward downstream, said flow passage having a substantially rectangular cross section,
    a straight capillary flow passage connected to said flow passage downstream thereof, said capillary flow passage having a substantially rectangular cross section,
    a second inlet for sample fluid,
    a nozzle communicating with said second inlet and opened within said flow passage in the same direction as the flow direction of said straight capillary flow passage,
    a discharge port provided at a terminal end of said straight capillary flow passage, and
    flow regulating means for regulating the flow of said sheath fluid in said straight capillary flow passage to be a laminar flow having a gradient of flow velocity, wherein said flow regulating means comprises a plurality of partition walls extended in said flow passage in the flow direction and dividing said flow passage into a plurality of divided flow passages of which flow resistance are made larger from a first side wall of said flow passage toward a second side wall opposite to said first side wall.

7. A sheath flow type flow-cell device for a flow-cytometer comprising:
    a first inlet for sheath fluid,
    a flow passage communicating with said first inlet and contracted toward downstream, said flow passage having a substantially rectangular cross section,
    a straight capillary flow passage connected to said flow passage downstream thereof, said capillary flow passage having opposing first and second side walls joined by top and bottom walls and having a substantially rectangular cross section,
    a second inlet for sample fluid which includes cells therein,
    a nozzle communicated with said second inlet and opened within said flow passage in the same direction as the flow direction of said straight capillary flow passage, a discharge port provided at a terminal end of said straight capillary flow passage, and flow regulating means for regulating the flow of said sheath fluid in said straight capillary flow passage to be a laminar flow having a gradient of flow velocity from said first side wall to said second said wall which is sufficient to flatten said cells in said sample fluid into a form symmetrical with respect to an axis thereof and having a longitudinal axis coinciding with said flow direction of said straight capillary flow passage.

8. A sheath flow type flow-cell device for a flow-cytometer comprising:

a first inlet for sheath fluid, a flow passage communicating with said first inlet and contracted toward downstream, said flow passage having a substantially rectangular cross section, a straight capillary flow passage connected to said flow passage downstream thereof, said capillary flow passage having a substantially rectangular cross section, a second inlet for sample fluid, a nozzle communicating with said second inlet and opened within said flow passage in the same direction as the flow direction of said straight capillary flow passage, a discharge port provided at a terminal end of said straight capillary flow passage, and flow regulating means for regulating the flow of said sheath fluid in said straight capillary flow passage to be a laminar flow having a gradient of flow velocity, wherein said flow regulating means regulates said flow of said sheath fluid in said straight capillary flow passage to be a laminar flow having a gradient of flow velocity increasing across said straight capillary flow passage from one side thereof to another side thereof opposite said one side.

9. A sheath flow type flow-cell device as claimed in claim 8, wherein said flow regulating means comprises a net member stretched across said flow passage upstream from the opening of said nozzle, the mesh of said net being minuter from a first side wall of said flow passage toward second side wall opposite to said first side wall.

* * * * *